United States Patent [19]
Yabiki et al.

[11] Patent Number: 5,478,559
[45] Date of Patent: Dec. 26, 1995

[54] METHOD AND COMPOSITION FOR INCREASING BODY WEIGHT AND STIMULATING IMMUNE SYSTEMS

[75] Inventors: Terutake Yabiki, Sakura; Atsushi Hamano, Inashiki; Sunao Fukami, Ichikawa; Katsuyoshi Kitajima, Sakura; Fumio Tachibana, Tsuchiura, all of Japan

[73] Assignee: National Federation of Agricultural Cooperative Associations, Tokyo, Japan

[21] Appl. No.: 642,049

[22] Filed: Jan. 15, 1991

[51] Int. Cl.$^6$ ............................ A61K 31/00; A61K 31/38
[52] U.S. Cl. .................................... 424/184.1; 424/234.1; 424/246.1; 424/244.1
[58] Field of Search ................................... 424/88, 93, 92

[56] References Cited

U.S. PATENT DOCUMENTS 4,271,147  6/1981  Helting et al. ............................ 424/88

OTHER PUBLICATIONS

Sasaki et al. (1987) Jpn. J. Vet. Sci. 49(2) 235–243.
Azuma et al. (1978) Cancer Immunol. Immunother. 4.95–100.
Yamamura et al. (1976) Gann, 67:669–677.
Zbar et al. (1974) Jour. of the National Cancer Instit. 52(5):1571–1577.
Zbar et al, "Immunotherapy of Cancer: Regression of Established Intradermal Tumors After Introlesional Injection of Mycobacterial Cell Walls Attached to Oil Droplets" J. National Cancer Institute, vol. 52, 1974, pp. 1571–1577.

*Primary Examiner*—Jill Warden
*Assistant Examiner*—S. Marshall
*Attorney, Agent, or Firm*—Birch, Stewart, Kolasch & Birch

[57] ABSTRACT

A method and composition for increasing body weight and stimulating the immune systems of domestic animals, poultry and fish are disclosed. In the method of the present invention, bacterial and yeast cells from which capsules have been removed are given to the domestic animals, poultry or fish.

15 Claims, No Drawings

METHOD AND COMPOSITION FOR INCREASING BODY WEIGHT AND STIMULATING IMMUNE SYSTEMS

BACKGROUND OF THE INVENTION

I. Field of the Invention

The present invention relates to a method and composition for increasing body weight and stimulating the immune systems of domestic animals poultry and fish, and to a feed comprising the same.

II. Description of the Related Art

Immune organs and immunocytes of domestic animals and poultry in infancy do not work very efficiently, so that infant domestic animals and poultry have innate immune disorders. Therefore, they are liable to suffer from infectious diseases which attack the digestive system or the respiratory system, such as scours or diarrhea, representing a serious problem in the livestock industry. For example, the rate of occurrence of scours in infant swine during the lactation period or ablactation period is as high as 40%–100%. The economic loss due to the death or developmental delay in infant swine suffering from diarrhea or white diarrhea is very large, and is a serious problem in the swine raising industry.

For the treatment or prophylaxis of such infectious diseases, various antibiotics and sulfa drugs are used. However, their effects are not always satisfactory and their use is being suppressed because of the problem of residual drugs and the generation of drug-resistant bacteria.

Thus, there is a great demand for a drug which prevents or cures infectious diseases of infant domestic animals and poultry, which is not a bactericide such as an antibiotic.

It was recently found that components separated from cell walls of microorganisms such as BCG(Bacillus Calmette-Guerin) and Norcadia have a stimulating or strengthening effect on the immune system, and that the effective components are peptide glycans ("Journal of National Cancer Institute", vol. 52, p. 1571, 1974; "Gann", vol. 69, p. 669, 1976; "Cancer Immunology and Immunotherapy", vol, 4, p. 95, 1978). Subsequent to this finding, Gram-positive bacteria which naturally and widely occur and which have no endotoxin have drawn much attention, and it was found that a peptide glycan obtained from a Gram-positive bacterium is effective in stimulating the immune system and increasing the body weight of infant swine ("Japanese Journal of Veterinary Science", vol. 49, p. 235, 1987).

The cell wall of a Gram-positive bacterium is a sack-like structure Constituted by a peptide glycan and a structure specific to the bacterium mainly composed of a polysaccharide or teichoic acid, which latter structure is covalently bonded to the peptide glycan. The cell wall contacts the outer surface of the cell membrane. The cell wall serves not only to retain the shape of the cell but also to protect the cell from various exogenous stimuli. In particular, the peptide glycan moiety is important not only for stimulating the immune system but also for retaining the shape of the cell. That is, the peptide glycan forms a large and extremely rigid polymer which constitutes a three-dimensional reticulose structure in which the glycan chain composed of N-acetylglucosamine and N-acetylmuramic acid, and the peptide chain, are bonded.

The cell walls are hitherto separated and extracted from bacteria by first removing the cytoplasmic components under specific conditions, recovering the crude cell walls remaining as a residue, and then treating the residue with a protease and a nuclease.

However, this conventional process is complicated and the yield is low. Therefore, cell walls prepared by the conventional process are too expensive as an additive in feed for domestic animals and poultry.

SUMMARY OF THE INVENTION

Accordingly, an object of the present invention is to provide effective means for increasing the body weight and strengthening the immune systems of domestic animals, poultry and fish.

The inventors intensively studied to discover that cells of bacteria or yeast from which capsules are removed exhibit excellent effects in increasing the body weight and for strengthening the immune system of domestic animals, poultry and fishes, especially the infants thereof, and to discover that the capsules may be removed by merely treating the cells with a surfactant, thereby completing the present invention.

That is, the present invention provides a weight-increasing and immunostimulating composition comprising bacterial or yeast cells from which capsules are removed in an amount effective for increasing body weight and stimulating the immune system.

The present invention also provides a method for increasing body weight and stimulating the immune systems of domestic animals, poultry and fishes comprising administering bacterial or yeast cells from which capsules are removed to said domestic animals, poultry and fishes in an amount effective for increasing the body weight and stimulating the immune system.

The present invention also provides a feed comprising bacterial or yeast cells from which capsules are removed.

Via the present invention, a novel composition and method for increasing body weight and stimulating the immune system of domestic animals, poultry and fish are provided. The composition and method of the present invention are especially effective for infants of domestic animals, poultry and fishes (hereinafter referred to as "domestic animals" for short). Further, the effective ingredient of the composition of the present invention may be obtained by merely treating the bacterial or yeast cells with a surfactant, so that enzyme treatment as employed in the prior art is not necessary. Thus, the effective ingredient may be produced in a much cheaper way than in the conventional composition. Therefore, the effective ingredient is economically viable as an additive to feed of domestic animals. By giving the effective ingredient to domestic animals, especially infants thereof, death due to diarrhea and developmental delay are avoided, so that the present invention will greatly contribute to the raising of domestic animals.

DETAILED DESCRIPTION OF THE PREFERRED EMBODIMENTS

As stated above, in the method for increasing body weight and stimulating the immune systems of domestic animals of the present invention, bacterial or yeast cells from which capsules are removed are employed as an effective ingredient. The bacteria or yeasts may be any bacteria or yeasts. Examples of the preferred bacteria include those belonging to the genus Bifidobacterium (such as *Bifidobacterium thermophilum*), those belonging to the genus Bacillus (such as *Bacillus subtilus*), those belonging to the genus Corynebacterium (such as *Corynebacterium ovis*), those belonging to the genus Actinomyces (such as *Actinomyces pyogenes*), those belonging to the genus Lactobacillus (such as *Lacto-

*bacillus acidophilus*), those belonging to the genus Streptococcus (such as *Streptococcus faecalis*) and those belonging to the genus Staphylococcus (such as *Staphylococcus chonii*). Examples of the preferred yeasts include those belonging to the genus Kluyveromyces (such as *Kluyveromyces lactis*) and those belonging to the genus Saccharomyces (such as *Saccharomyces cerevisiae*). Among these bacteria and yeasts, bacteria belonging to the genus Bifidobacterium are most preferred.

The bacterial or yeast cells to be given to the domestic animals may be alive or dead.

The effective ingredient may be produced by treating the cells with a surface active agent, and no enzyme treatment or the like is necessary. The treatment with the surfactant may be carried out by suspending the cells in a surfactant solution or by suspending the cells in water or a buffer solution and then adding a surfactant thereto.

Although any surface active agent may be employed, nonionic surfactants are preferred because they may be comparatively easily removed in later steps. Commercially available nonionic surfactants such as Tween 20 and Triton X-100 may be conveniently employed.

In cases where the cells are treated in a surfactant solution, the concentration of the surfactant may preferably be 0.05–5% (v/v), more preferably 0.1–1.5% (v/v). The weight of the surfactant solution may preferably be 1–10 times 50–100 g of the wet cells (cells collected by centrifugation at 3000–8000 rpm for 10–60 minutes), or 10–100 times 50–100 g of the dry cells. In cases where the cells are preliminarily suspended in water or a buffer, the surfactant may be added in the amount just described above.

The treatment with the surfactant may be carried out at room temperature or at an elevated temperature of 30°–60° C. The treatment time may preferably be 1–24 hours. It is preferred to stir the suspension during the treatment.

After the treatment, in order to remove the surfactant remaining on the cells, it is preferred to wash the cells with water or a buffer by centrifugation or filtration.

It is known that bacteria cells are autolyzed by their autolytic enzymes (Masaru FUNATSU and Onori TSURU, "Bacteriolytic Enzymes" p. 14, Kodansha, 1977). Therefore, it is preferred to inactivate the autolytic enzymes before the treatment with the surfactant. The inactivation of the autolytic enzymes may be carried out by heating the cells. The conditions of the heat treatment should be selected so as to completely inactivate the autolytic enzymes while not significantly denaturing the proteins of the cells. Thus, the conditions of the heat treatment may preferably be 56°–75° C. for 15–60 minutes, or 10 minutes in boiling water.

It should be noted that the removal of the capsules from the cells does not necessarily require the use of a surfactant. Capsules of some bacteria or yeasts may be removed by merely stirring or shaking cell suspensions. In such cases, the effective ingredient to be used in the present invention may readily be obtained by stirring or shaking the cell suspension without using a surfactant.

The bacteria or yeasts cells from which the capsules are removed may be used as they are. Alternatively, lyophilized cells from which the capsules have been removed may be given to the domestic animals.

The composition and method of the present invention are effective for increasing the body weight and stimulating the immune systems of domestic animals such as swine, bovines, horses, goats, dogs, cats and rodents; poultry such as chickens; and fishes and shell fishes including freshwater fishes such as carp, rainbow trout, ayu, eel, terapia, conger, salmon and trout, and saltwater fishes such as porgy, yellowtail, flounder, globe fish and prawn. The composition and method of the present invention are especially effective for infant domestic animals, i.e., 2–3 months old.

The decapsulated cells may be added to feed as they are, or a suspension of the cells in water may be orally administered to the domestic animals. Alternatively, the decapsulated cells may be admixed with a conventional vehicle to form the composition of the present invention, and the composition may be added to the feed after drying.

The dose of the decapsulated cells administered to the domestic animals is usually 10 μg to 1 mg per day per 1 kg of the body weight.

The present invention will now be described by way of examples thereof. It should be noted that these Examples are presented for illustration purposes only, and should not be interpreted in any restrictive way.

EXAMPLE 1

Production of Decapsulated Bacterial Cells

*Bifidobacterium thermophilum* PNA 1–24, obtained from Rikagaku Kenkyujo, was cultured, and 100 g (wet weight) of the cultured cells were suspended in 1 liter of 0.05M phosphate buffer (pH 7.0). The suspension was heated at 75° C. for 30 minutes to inactivate the autolytic enzymes of the cells. A surfactant (Tween 20) was added to the suspension to a final concentration of 0.5% (v/v), and the resultant was stirred at room temperature for 12–15 hours, followed by centrifugation at 8000 rpm for 20 minutes. The thus treated cells were then washed three times by centrifugation, and the collected cells were lyophilized to obtain 12 g of lyophilized cells. The lyophilized cells were used as a feed additive in the subsequent Examples.

EXAMPLE 2

Analysis of Decapsulated Cells

Whether or not the lyophilized decapsulated Bifidobacterium cells prepared in Example 1 contain hexosamine (major components of which are N-acetylglucosamine and N-acetylmuramic acid), which is an immunostimulating agent, was determined. Reduced saccharides of the cells were also analyzed.

The analysis of the hexosamine was carried out according to the Morgan-Elson method and the Dische-Bordenfreund method (indole-hydrochloric acid method). The measured contents of the hexosamine were 2.74% and 3.84%, respectively. The reduced saccharides were quantified by the phenol sulfuric acid method. The content of the reduced saccharides was 13.4%. As is apparent from these results, the decapsulated cells prepared in Example 1 contained hexosamine, which is an immunostimulating agent.

EXAMPLE 3

Effect in Preventing Scours and Increasing the Body Weight of Infant Swine

The lyophilized decapsulated cells obtained in Example 1 (hereinafter referred to as "the feed additive" for short) were added to the feed during the early lactation period for swine, and the feed was given to infant swine. Whether the scours of infant swine was reduced and whether the body weight of the infant swine was increased were determined.

More particularly, to the feed during the early lactation period of swine, 1 ppm of the feed additive was added and the obtained feed was given to the treated group (8 animals) from 3 weeks to 5 weeks after birth. To the control group (6 animals), feed during the early lactation period of swine to which the feed additive was not added was given. To the animals in both groups, after 5 weeks from birth, feed for the late lactation period was given until 9 weeks after birth. The body weight of the animals, as well as the scours score, was determined. The scours score was calculated according to the following equation:

$$\text{Scours Score} = \frac{P}{T \times N}$$

(wherein P represents the total feces points of all animals in each group, T represents the time period of the test (days), and N represents the number of animals in the group).

The feces point was assigned to the feces such that no point was given to normal feces, 1 point was given to soft feces, 2 points were given to mud-like feces and 3 points were given to liquid-like feces. As is apparent from this definition, the higher the scours score, the more severe the scours.

The results are shown in Table 1. As is apparent from Table 1, the scours in the animals in the treated group was much less severe than in the animals in the control group. Further, the body weight of the animals in the treated group was greater than that in the control group.

of the swine were strengthened or not was determined by histoimmunologically examining the enteric canals of the animals.

The number of sacrificed animals was two in the treated group and one in the control group, at each time of the completion of giving feeds for the early and late lactation periods. The plasma cells which produce immunoglobulins were stained by the pyronin methyl green staining method, and the IgA-containing cells which are important for topical immunity of the enteric canal were stained by the PAP method. The number of plasma cells and IgA-containing cells was counted by observing the cells with a microscope with a magnification of 400×20.

The results are ! shown in Table 2. As can be seen from Table 2, at the completion of giving the feed during the early lactation period (i.e., 5 weeks after birth), the number of plasma cells in duodenums and jejunums of the animals in the treated group was apparently larger than that in the animals in the control group. The number of IgA-containing cells in duodenums and jejunums was also larger in the treated group than in the control group.

At the time of completion of giving the feed for the late lactation period (i.e., 9 weeks after birth), the number of plasma cells in duodenums, jejunums and ileums of the animals in the treated group was larger than that of the animals in the control group. The number of IgA-containing cells in duodenums and jejunums was also larger in the treated group than in the control group (Table 3).

TABLE 1

Increase in Body Weight of Infant Swine and Preventive Effect on Scours

| | Control Group | | | Treated Group | | |
| --- | --- | --- | --- | --- | --- | --- |
| | Early Period | Late Period | | Early Period | Late Period | |
| Item | 3–5 Weeks Old | 5–7 Weeks Old | 7–9 Weeks Old | 3–5 Weeks Old | 5–7 Weeks Old | 7–9 Weeks Old |
| Increase in Body Weight (g/Day · Head) | 79 (100) | 445 (100) | 688 (100) | 147 (186) | 435 (98) | 773 (112) |
| Scours Score (Score/Day · Head) | 1.20 | 0 | 0.02 | 0.13 | 0 | 0 |

EXAMPLE 4

Effect in Stimulating the Immune System in Enteric Canal Tissues

The animals in the treated group and the control group tested in Example 3 were sacrificed at the time of completion of giving feed during the early lactation period of swine (i.e., 5 weeks after birth) or at the time of completion of giving feed during the late lactation period of swine (i.e., 9 weeks after birth), and anatomized. Whether the immune systems From these results, it was confirmed that the enteric canal tissues of the infant swine to which the feed of the present invention containing the decapsulated cells had more antibody-producing cells than the infant swine to which the ordinary feed was given, so that their immunity in the enteric canals was strengthened.

TABLE 2

Number of Cells Producing Ig intestine Laminapropia Mucosae of Infant Swine
(at the Time of Completion of Giving Feed during the Early Lactation Period of Swine)

| | | Number of Plasma Cells | | | Number of Cells Having IgA | | |
| --- | --- | --- | --- | --- | --- | --- | --- |
| | Swine No. | Duodenum | Jejunum | Ileum | Duodenum | Jejunum | Ileum |
| Treated Group | 11 | 2367 | 598 | 338 | 437 | 253 | 95 |
| | 12 | 1673 | 677 | 232 | 363 | 264 | 94 |

TABLE 2-continued

Number of Cells Producing Ig intestine Laminapropia Mucosac of Infant Swine
(at the Time of Completion of Giving Feed during the Early Lactation Period of Swine)

|  | Swine No. | Number of Plasma Cells | | | Number of Cells Having IgA | | |
| --- | --- | --- | --- | --- | --- | --- | --- |
|  |  | Duodenum | Jejunum | Ileum | Duodenum | Jejunum | Ileum |
| Control Group | 6 | 744 | 388 | 240 | 171 | 235 | 112 |

TABLE 3

Number of Cells Producing Ig in Intestine Laminapropia Mucosae of Infant Swine
(at the Time of Completion of Giving Feed during the Late Lactation Stage of Swine)

|  | Swine No. | Number of Plasma Cells | | | Number of Cells Having IgA | | |
| --- | --- | --- | --- | --- | --- | --- | --- |
|  |  | Duodenum | Jejunum | Ileum | Duodenum | Jejunum | Ileum |
| Treated Group | 7 | 3664 | 1639 | 1098 | 1215 | 865 | 224 |
|  | 8 | 3959 | 1775 | 1037 | 1026 | 943 | 309 |
| Control Group | 10 | 2532 | 1350 | 640 | 773 | 593 | 250 |

EXAMPLE 5

Immunostimulating Effect in Mice

After intraperitoneally administering the lyophilized decapsulated cells obtained in Example 1 to mice, the mice were attacked by *E. coli* (septic type) or by *Salmonella typhimurium*, ATCC 1311. The effect of the decapsulated cells was evaluated according to the survival rate.

More particularly, 5 mice (ICR series) were involved in each of the treated groups and the control groups. The lyophilized decapsulated cells were intraperitoneally administered 4 days and 1 day before the attack by *E. coli*, or 4 days before the attack by *Salmonella typhimurium*. The administered *E. coli* was $1.8 \times 10^8$ CFU/animal and the administered *Salmonella typhirium* was $3.4 \times 10^7$ CFU/animal.

The results are shown in Table 4. As can be seen from Table 4, the decapsulated cells were very effective against the attack by *E. coli*. As for the attack by *S. typhirium*, although no effect was observed in the group treated with 40 μg of the cells, the administration of the decapsulated cells was significantly effective in the groups treated with 200 μg or more of the cells. The animals in the control group to which the decapsulated cells were not administered were eradicated 1–5 days after the attack by *E. coli* or *S. typhirium*. The immunostimulating effect was calculated according to the following equation:

$$(A-B)/C \times 100\%$$

(wherein A represents the number of surviving animals in the treated group, B represents the number of surviving animals in the control group and C represents the number of the animals in the treated group). The immunostimulating effect was evaluated according to the following criteria, the evaluation being shown in Table 4:

⊙ (≧75%, very effective)
○ (50–75%, effective)
△ (25–50%, slightly effective)
X (≦25%, ineffective)

From these results, it was confirmed that the decapsulated cells exhibit a strong immunostimulating effect sufficiently effective against strongly virulent microorganisms such as *E. coli* and *S. typhirium*.

TABLE 4

Immunostimulating Effect in Mice

| Dose (μg/Head/Dosage) | Immunostimulating Effect | |
| --- | --- | --- |
|  | *E. coli* Attack (Intraperitoneal) | *S. typhimurium* Attack (Intraperitoneal) |
| 40 | ⊙ | x |
| 200 | ⊙ | o |
| 1000 | ⊙ | o |

We claim:

1. A composition, comprising as an effective ingredient cells of *Bifidobacterium thermophilum* or *Actinomyces pyogenes* from which capsules have been removed, in an amount effective for increasing body weight and stimulating the immune system, and a carrier selected from the group consisting of feed, water, and a conventional vehicle.

2. The composition of claim 1, wherein said effective ingredient is prepared by treating said cells with a surface active agent.

3. The composition of claim 1, wherein said cells are alive or dead.

4. The composition of claim 1, wherein said *Bifidobacterium thermophilum* is *Bifidobacterium thermophilum* PNA 1-24.

5. The composition of claim 1, wherein said carrier is feed.

6. The composition of claim 2, wherein said surface active agent is a nonionic surface active agent.

7. The composition of claim 5, wherein said cells are alive or dead.

8. The composition of claim 5, wherein said *Bifidobacterium thermophilum* is *Bifidobacterium thermophilum* PNA 1-24.

9. A method for increasing body weight and stimulating the immune system of domestic animals, poultry and fishes, comprising administering cells of *Bifidobacterium thermo-*

*philum* or *Actinomyces pyogenes* from which capsules have been removed to said domestic animals, poultry and fishes in an amount effective for increasing the body weight and stimulating the immune systems.

10. The method of claim 9, wherein said cells are alive or dead.

11. The method of claim 9, wherein said *Bifidobacterium thermophilum* is *Bifidobacterium thermophilum* PNA 1–24.

12. The method of claim 9 wherein decapsulated cells are administered in an amount of from 10 μg/kg body weight/day to 1 mg/kg body weight/day.

13. The method of claim 9, wherein said administering is conducted during the period when said domestic animals, poultry, and fishes are infants.

14. A method for increasing body weight and stimulating the immune system of swine, comprising administering feed containing 1 ppm of lyophilized, decapsulated cells of *Bifidobacterium thermophilum* PNA 1–24 to infant swine during the early lactation period from 3 weeks to 5 weeks after birth.

15. The method of claim 9, wherein said administering is conducted by adding decapsulated cells to feed, orally administering a suspension of said cells in water, or admixing decapsulated cells with a conventional vehicle and adding the admixture to feed after drying.

* * * * *